(12) United States Patent
SChneider et al.

(10) Patent No.: US 9,877,823 B2
(45) Date of Patent: Jan. 30, 2018

(54) CORNEAL IMPLANT RETAINING DEVICES AND METHODS OF USE

(71) Applicant: REVISION OPTICS, INC., Lake Forest, CA (US)

(72) Inventors: Ned SChneider, Aliso Viejo, CA (US); Alan Ngoc Le, Lake Forest, CA (US); Gregg Edmond Plambeck, Aliso Viejo, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 0 days.

(21) Appl. No.: 14/998,899

(22) Filed: Mar. 1, 2016

(65) Prior Publication Data

US 2016/0184085 A1    Jun. 30, 2016

Related U.S. Application Data

(62) Division of application No. 13/549,007, filed on Jul. 13, 2012, now Pat. No. 9,271,828.

(60) Provisional application No. 61/535,819, filed on Sep. 16, 2011.

(51) Int. Cl.
*A61F 9/00* (2006.01)
*A61F 2/14* (2006.01)

(52) U.S. Cl.
CPC .............. *A61F 2/148* (2013.01); *A61F 2/142* (2013.01)

(58) Field of Classification Search
CPC ...... A61F 2/148; A61F 2/1662; A61F 2/1675; A61F 2/1691
See application file for complete search history.

(56) References Cited

U.S. PATENT DOCUMENTS

| | | |
|---|---|---|
| 2,521,161 A | 9/1950 | Grover |
| 2,714,721 A | 8/1955 | Stone, Jr. |
| 3,091,328 A | 5/1963 | Leonardos |
| 3,168,100 A | 2/1965 | Rich |
| 3,305,235 A | 2/1967 | Williams |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |
| 3,996,627 A | 12/1976 | Deeg et al. |
| 4,030,480 A | 6/1977 | Meyer |

(Continued)

FOREIGN PATENT DOCUMENTS

| | | |
|---|---|---|
| DE | 3208729 A1 | 9/1983 |
| EP | 0308077 A2 | 3/1989 |

(Continued)

OTHER PUBLICATIONS

Alio, J. J., et al., "Intracorneal Inlay Complicated by Intrastomal Epithelial Opacification," Arch Ophthalmol, Oct. 2004; vol. 122; 6 pages.

(Continued)

*Primary Examiner* — Ashley Fishback
(74) *Attorney, Agent, or Firm* — Shay Glenn LLP

(57) ABSTRACT

Corneal implant retaining devices and their methods of use. The retaining devices can be a cap adapted to be disposed over a portion of a corneal implant insertion device.

17 Claims, 17 Drawing Sheets

(56) References Cited

U.S. PATENT DOCUMENTS

| | | |
|---|---|---|
| 4,037,604 A | 7/1977 | Newkirk |
| 4,037,866 A * | 7/1977 | Price .................... A61F 9/0061 294/1.2 |
| 4,039,827 A | 8/1977 | Zdrok et al. |
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,263,054 A | 4/1981 | Giambalvo |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,573,998 A | 3/1986 | Mazzocco |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,865,552 A | 9/1989 | Maloney et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,912 A | 6/1992 | Kaplan et al. |
| 5,123,921 A | 6/1992 | Werblin et al. |
| 5,139,518 A | 8/1992 | White |
| 5,163,934 A | 11/1992 | Munnerlyn |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst et al. |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,352,233 A | 10/1994 | Anis |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,407,241 A | 4/1995 | Harrison |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,487,377 A | 1/1996 | Smith et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |
| 5,601,584 A | 2/1997 | Obagi et al. |

(56) References Cited

U.S. PATENT DOCUMENTS

| | | | |
|---|---|---|---|
| 5,616,148 A * | 4/1997 | Eagles | A61F 2/167 606/107 |
| 5,620,450 A | 4/1997 | Eagles et al. | |
| 5,628,794 A | 5/1997 | Lindstrom | |
| 5,630,810 A | 5/1997 | Machat | |
| 5,634,943 A | 6/1997 | Villain et al. | |
| 5,643,276 A | 7/1997 | Zaleski | |
| 5,647,865 A | 7/1997 | Swinger | |
| 5,657,108 A | 8/1997 | Portney | |
| 5,682,223 A | 10/1997 | Menezes et al. | |
| 5,684,560 A | 11/1997 | Roffman et al. | |
| 5,715,031 A | 2/1998 | Roffman et al. | |
| 5,716,633 A | 2/1998 | Civerchia | |
| 5,722,948 A | 3/1998 | Gross | |
| 5,722,971 A | 3/1998 | Peyman | |
| 5,728,155 A | 3/1998 | Anello et al. | |
| 5,732,990 A | 3/1998 | Yavitz et al. | |
| 5,752,928 A | 5/1998 | de Roulhac et al. | |
| 5,755,785 A | 5/1998 | Rowsey et al. | |
| 5,766,181 A | 6/1998 | Chambers et al. | |
| 5,772,667 A | 6/1998 | Blake | |
| 5,779,711 A | 7/1998 | Kritzinger et al. | |
| 5,785,674 A | 7/1998 | Mateen | |
| 5,800,442 A | 9/1998 | Wolf et al. | |
| 5,800,529 A | 9/1998 | Brauker et al. | |
| 5,805,260 A | 9/1998 | Roffman et al. | |
| 5,810,833 A | 9/1998 | Brady et al. | |
| 5,817,115 A | 10/1998 | Nigam | |
| 5,824,086 A | 10/1998 | Silvestrini | |
| 5,847,802 A | 12/1998 | Menezes et al. | |
| 5,855,604 A | 1/1999 | Lee | |
| 5,860,984 A | 1/1999 | Chambers et al. | |
| 5,872,613 A | 2/1999 | Blum et al. | |
| 5,873,889 A | 2/1999 | Chin | |
| 5,876,439 A | 3/1999 | Lee | |
| 5,888,243 A | 3/1999 | Silverstrini | |
| 5,893,719 A | 4/1999 | Radow | |
| 5,913,898 A | 6/1999 | Feingold | |
| 5,919,185 A | 7/1999 | Peyman | |
| 5,928,245 A | 7/1999 | Wolf et al. | |
| 5,929,968 A | 7/1999 | Cotie et al. | |
| 5,929,969 A | 7/1999 | Roffman | |
| 5,935,140 A | 8/1999 | Buratto | |
| 5,941,583 A | 8/1999 | Raimondi | |
| 5,944,752 A | 8/1999 | Silvestrini | |
| 5,945,498 A | 8/1999 | Hopken et al. | |
| 5,964,748 A | 10/1999 | Peyman | |
| 5,964,776 A | 10/1999 | Peyman | |
| 5,968,065 A | 10/1999 | Chin | |
| 5,976,150 A | 11/1999 | Copeland | |
| 5,976,168 A | 11/1999 | Chin | |
| 5,980,549 A | 11/1999 | Chin | |
| 6,007,510 A | 12/1999 | Nigam | |
| 6,010,510 A | 1/2000 | Brown et al. | |
| 6,024,448 A | 2/2000 | Wu et al. | |
| 6,033,395 A | 3/2000 | Peyman | |
| 6,036,714 A | 3/2000 | Chin | |
| 6,050,999 A | 4/2000 | Paraschac et al. | |
| 6,055,990 A | 5/2000 | Thompson | |
| 6,059,775 A | 5/2000 | Nielsen | |
| 6,066,170 A | 5/2000 | Lee | |
| 6,068,642 A | 5/2000 | Johnson et al. | |
| 6,079,826 A | 6/2000 | Appleton et al. | |
| 6,083,231 A | 7/2000 | Van Noy et al. | |
| 6,086,202 A | 7/2000 | Chateau et al. | |
| 6,090,141 A | 7/2000 | Lindstrom | |
| 6,102,946 A | 8/2000 | Nigam | |
| 6,110,166 A | 8/2000 | Juhasz et al. | |
| 6,120,148 A | 9/2000 | Fiala et al. | |
| 6,125,294 A | 9/2000 | Scholl et al. | |
| 6,129,733 A | 10/2000 | Brady et al. | |
| 6,139,560 A | 10/2000 | Kremer | |
| 6,142,969 A | 11/2000 | Nigam | |
| 6,143,001 A | 11/2000 | Brown et al. | |
| 6,159,241 A | 12/2000 | Lee et al. | |
| 6,171,324 B1 | 1/2001 | Cote et al. | |
| 6,175,754 B1 | 1/2001 | Scholl et al. | |
| RE37,071 E | 2/2001 | Gabrielian et al. | |
| 6,183,513 B1 | 2/2001 | Guenthner et al. | |
| 6,197,019 B1 | 3/2001 | Peyman | |
| 6,197,057 B1 | 3/2001 | Peyman et al. | |
| 6,197,058 B1 | 3/2001 | Portney | |
| 6,203,538 B1 | 3/2001 | Peyman | |
| 6,203,549 B1 | 3/2001 | Waldock | |
| 6,203,557 B1 | 3/2001 | Chin | |
| 6,206,919 B1 | 3/2001 | Lee | |
| 6,210,005 B1 | 4/2001 | Portney | |
| 6,214,015 B1 | 4/2001 | Reich et al. | |
| 6,214,044 B1 | 4/2001 | Silverstrini | |
| 6,217,571 B1 | 4/2001 | Peyman | |
| 6,221,067 B1 | 4/2001 | Peyman | |
| 6,228,113 B1 | 5/2001 | Kaufman | |
| 6,228,114 B1 | 5/2001 | Lee | |
| 6,248,111 B1 | 6/2001 | Glick et al. | |
| 6,250,757 B1 | 6/2001 | Roffman et al. | |
| 6,251,114 B1 | 6/2001 | Farmer et al. | |
| 6,264,648 B1 | 7/2001 | Peyman | |
| 6,264,670 B1 | 7/2001 | Chin | |
| 6,264,692 B1 | 7/2001 | Woffinden et al. | |
| 6,267,768 B1 | 7/2001 | Deacon et al. | |
| 6,271,281 B1 | 8/2001 | Liao et al. | |
| 6,277,137 B1 | 8/2001 | Chin | |
| 6,280,449 B1 | 8/2001 | Blake | |
| 6,280,470 B1 | 8/2001 | Peyman | |
| 6,283,595 B1 | 9/2001 | Breger | |
| 6,302,877 B1 | 10/2001 | Ruiz | |
| 6,325,509 B1 | 12/2001 | Hodur et al. | |
| 6,325,792 B1 | 12/2001 | Swinger et al. | |
| 6,350,272 B1 | 2/2002 | Kawesch | |
| 6,361,560 B1 | 3/2002 | Nigam | |
| 6,364,483 B1 | 4/2002 | Grossinger et al. | |
| 6,371,960 B2 | 4/2002 | Heyman et al. | |
| 6,391,230 B1 | 5/2002 | Sarbadhikari | |
| 6,398,277 B1 | 6/2002 | McDonald | |
| 6,398,789 B1 | 6/2002 | Capetan | |
| 6,428,572 B2 | 8/2002 | Nagai | |
| 6,435,681 B2 | 8/2002 | Portney | |
| 6,436,092 B1 | 8/2002 | Peyman | |
| 6,447,519 B1 | 9/2002 | Brady et al. | |
| 6,447,520 B1 | 9/2002 | Ott et al. | |
| 6,458,141 B1 | 10/2002 | Peyman | |
| 6,461,384 B1 | 10/2002 | Hoffmann et al. | |
| 6,471,708 B2 | 10/2002 | Green | |
| 6,474,814 B1 | 11/2002 | Griffin | |
| 6,506,200 B1 | 1/2003 | Chin | |
| 6,511,178 B1 | 1/2003 | Roffman et al. | |
| 6,527,389 B2 | 3/2003 | Portney | |
| 6,537,283 B2 | 3/2003 | Van Noy | |
| 6,543,610 B1 | 4/2003 | Nigam | |
| 6,544,286 B1 | 4/2003 | Perez | |
| 6,551,307 B2 | 4/2003 | Peyman | |
| 6,554,424 B1 | 4/2003 | Miller et al. | |
| 6,554,425 B1 | 4/2003 | Roffman et al. | |
| 6,557,998 B2 | 5/2003 | Portney | |
| 6,581,993 B2 | 6/2003 | Nigam | |
| 6,582,076 B1 | 6/2003 | Roffman et al. | |
| 6,589,057 B1 | 7/2003 | Keenan et al. | |
| 6,589,203 B1 | 7/2003 | Mitrev | |
| 6,589,280 B1 | 7/2003 | Koziol | |
| 6,592,591 B2 | 7/2003 | Polla et al. | |
| 6,596,000 B2 | 7/2003 | Chan et al. | |
| 6,605,093 B1 | 8/2003 | Blake | |
| 6,607,537 B1 | 8/2003 | Binder | |
| 6,607,556 B1 | 8/2003 | Nigam | |
| 6,623,522 B2 | 9/2003 | Nigam | |
| 6,626,941 B2 | 9/2003 | Nigam | |
| 6,629,979 B1 | 10/2003 | Feingold et al. | |
| 6,632,244 B1 | 10/2003 | Nigam | |
| 6,641,577 B2 | 11/2003 | Bille | |
| 6,645,246 B1 | 11/2003 | Weinschenk, III et al. | |
| 6,648,877 B1 | 11/2003 | Juhasz et al. | |
| 6,657,029 B2 | 12/2003 | Vanderbilt | |
| 6,666,887 B1 | 12/2003 | Callahan et al. | |
| 6,673,112 B2 | 1/2004 | Nigam | |

(56) References Cited

U.S. PATENT DOCUMENTS

| | | |
|---|---|---|
| 6,702,807 B2 | 3/2004 | Peyman |
| 6,709,103 B1 | 3/2004 | Roffman et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,733,526 B2 | 5/2004 | Paul et al. |
| 6,740,078 B2 | 5/2004 | Tamayo |
| 6,808,262 B2 | 10/2004 | Chapoy et al. |
| 6,824,178 B2 | 11/2004 | Nigam |
| 6,849,090 B2 | 2/2005 | Nigam |
| 6,855,163 B2 | 2/2005 | Peyman |
| 6,875,232 B2 | 4/2005 | Nigam |
| 6,879,402 B2 | 4/2005 | Küchel |
| 6,881,197 B1 | 4/2005 | Nigam |
| 6,893,461 B2 | 5/2005 | Nigam |
| 6,949,093 B1 | 9/2005 | Peyman |
| 6,955,432 B2 | 10/2005 | Graham |
| 7,128,351 B2 | 10/2006 | Nigam |
| 7,585,075 B2 | 9/2009 | Marmo |
| 7,699,837 B2 | 4/2010 | Cox et al. |
| 7,776,086 B2 | 8/2010 | Miller |
| 7,976,577 B2 | 7/2011 | Silvestrini |
| 7,992,906 B2 | 8/2011 | Nigam |
| 8,057,541 B2 | 11/2011 | Dishler et al. |
| 8,162,953 B2 | 4/2012 | Dishler et al. |
| 8,469,948 B2 | 6/2013 | Dishler et al. |
| 8,540,727 B2 | 9/2013 | Dishler et al. |
| 8,668,735 B2 | 3/2014 | Nigam et al. |
| 8,685,292 B2 | 4/2014 | Mandler et al. |
| 8,900,296 B2 | 12/2014 | Holliday et al. |
| 9,005,280 B2 | 4/2015 | Nigam |
| 9,271,828 B2 | 3/2016 | Schneider et al. |
| 2001/0027314 A1 | 10/2001 | Peyman |
| 2001/0031959 A1 | 10/2001 | Rozakis et al. |
| 2001/0051826 A1 | 12/2001 | Bogaert et al. |
| 2002/0010510 A1 | 1/2002 | Silvestrini |
| 2002/0055753 A1 | 5/2002 | Silvestrini |
| 2002/0063068 A1 | 5/2002 | Faxe |
| 2002/0101563 A1 | 8/2002 | Miyamura et al. |
| 2002/0103538 A1 | 8/2002 | Hughes et al. |
| 2002/0138069 A1 | 9/2002 | Peyman |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0176855 A1 | 9/2003 | Gross et al. |
| 2003/0208190 A1 | 11/2003 | Roberts et al. |
| 2003/0220653 A1 | 11/2003 | Perez |
| 2003/0229303 A1 | 12/2003 | Haffner et al. |
| 2004/0010278 A1 | 1/2004 | Nakamura et al. |
| 2004/0019379 A1 | 1/2004 | Glick et al. |
| 2004/0034413 A1 | 2/2004 | Christensen |
| 2004/0054408 A1 | 3/2004 | Glick et al. |
| 2004/0059320 A1 | 3/2004 | Telandro et al. |
| 2004/0073303 A1 | 4/2004 | Schanzlin |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0182488 A1 | 8/2005 | Peyman |
| 2005/0203494 A1 | 9/2005 | Holliday |
| 2005/0222679 A1 | 10/2005 | Peyman |
| 2005/0246016 A1 | 11/2005 | Miller et al. |
| 2005/0261752 A1 | 11/2005 | Chernyak |
| 2006/0004381 A1 | 1/2006 | Feingold et al. |
| 2006/0020267 A1 | 1/2006 | Marmo |
| 2006/0105309 A1 | 5/2006 | Stoll et al. |
| 2006/0116762 A1 | 6/2006 | Hong et al. |
| 2006/0134170 A1 | 6/2006 | Griffith et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0038276 A1 | 2/2007 | Yaldo |
| 2007/0106318 A1 | 5/2007 | McDonald |
| 2007/0106376 A1 | 5/2007 | Roberts et al. |
| 2007/0129797 A1 | 6/2007 | Lang et al. |
| 2007/0182920 A1 | 8/2007 | Back et al. |
| 2007/0244559 A1 | 10/2007 | Shiuey |
| 2007/0255401 A1 | 11/2007 | Lang |
| 2007/0270945 A1* | 11/2007 | Kobayashi ............ A61F 2/1664 623/6.12 |
| 2007/0280994 A1 | 12/2007 | Cunanan |
| 2008/0039825 A1 | 2/2008 | Lai et al. |
| 2008/0228177 A1 | 9/2008 | Moritz et al. |
| 2008/0262610 A1 | 10/2008 | Lang et al. |
| 2008/0269771 A1 | 10/2008 | Fulcher |
| 2008/0275433 A1 | 11/2008 | Russmann et al. |
| 2008/0281304 A1 | 11/2008 | Campbell |
| 2009/0005764 A1 | 1/2009 | Knox et al. |
| 2009/0079940 A1 | 3/2009 | Dai et al. |
| 2009/0216217 A1 | 8/2009 | Odrich et al. |
| 2009/0326650 A1 | 12/2009 | Zickler et al. |
| 2010/0069915 A1 | 3/2010 | Shiuey |
| 2010/0210996 A1 | 8/2010 | Peyman |
| 2010/0241060 A1 | 9/2010 | Roizman et al. |
| 2010/0331830 A1 | 12/2010 | Bischoff et al. |
| 2010/0331831 A1 | 12/2010 | Bischoff et al. |
| 2011/0029073 A1 | 2/2011 | Liang |
| 2011/0149241 A1 | 6/2011 | Dai |
| 2011/0172675 A1 | 7/2011 | Danta et al. |
| 2011/0208300 A1 | 8/2011 | de Juan et al. |
| 2011/0218623 A1 | 9/2011 | Dishler et al. |
| 2011/0256806 A1 | 10/2011 | Monnoyeur |
| 2011/0290681 A1 | 12/2011 | Nigam |
| 2011/0319876 A1 | 12/2011 | Feingold |
| 2012/0231416 A1 | 9/2012 | Drapeau et al. |
| 2012/0238806 A1 | 9/2012 | Mangiardi et al. |
| 2012/0245592 A1 | 9/2012 | Berner et al. |
| 2012/0245683 A1 | 9/2012 | Christie et al. |
| 2013/0060255 A1 | 3/2013 | Feingold et al. |
| 2013/0211523 A1 | 8/2013 | Southard et al. |
| 2013/0231739 A1 | 9/2013 | Dishler et al. |
| 2013/0253527 A1 | 9/2013 | Schneider et al. |
| 2013/0253529 A1 | 9/2013 | Walter et al. |
| 2013/0281993 A1 | 10/2013 | Dishler et al. |
| 2013/0317605 A1 | 11/2013 | Ide et al. |
| 2013/0324983 A1 | 12/2013 | Liang |
| 2013/0331935 A1 | 12/2013 | Krause et al. |
| 2014/0135915 A1 | 5/2014 | Nigam et al. |
| 2014/0200665 A1 | 7/2014 | Lang et al. |
| 2014/0257477 A1 | 9/2014 | Plambeck et al. |
| 2015/0080865 A1 | 3/2015 | Holliday et al. |
| 2015/0250652 A1 | 9/2015 | Holliday et al. |
| 2015/0297340 A1 | 10/2015 | Esguerra et al. |
| 2015/0366657 A1 | 12/2015 | Sharma |
| 2015/0375355 A1 | 12/2015 | Collins et al. |
| 2016/0051359 A1 | 2/2016 | Esguerra et al. |
| 2016/0331517 A1 | 11/2016 | Dishler et al. |
| 2017/0128193 A1 | 5/2017 | Schneider et al. |
| 2017/0143544 A1 | 5/2017 | Holliday et al. |
| 2017/0189166 A1 | 7/2017 | Holliday |
| 2017/0249871 A1 | 8/2017 | Le |

FOREIGN PATENT DOCUMENTS

| | | |
|---|---|---|
| EP | 0420549 A2 | 4/1991 |
| EP | 0729323 B1 | 7/1998 |
| EP | 0668061 B1 | 9/2000 |
| JP | S5973622 A | 4/1984 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2001091910 A | 4/2001 |
| JP | 2002537895 | 11/2002 |
| JP | 03-508135 | 3/2003 |

(56) References Cited

FOREIGN PATENT DOCUMENTS

| | | |
|---|---|---|
| JP | 2007500070 | 1/2007 |
| JP | 2010507814 A | 3/2010 |
| JP | 2010220488 A | 10/2010 |
| JP | 2012523854 A | 10/2012 |
| KR | 2001-0013218 | 2/2001 |
| RU | 2294722 C2 | 3/2007 |
| WO | WO92/08423 A1 | 5/1992 |
| WO | WO93/05731 A1 | 4/1993 |
| WO | WO96/26690 A1 | 9/1996 |
| WO | WO98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO2005/082265 A1 | 9/2005 |
| WO | WO 2005/107648 A2 | 11/2005 |
| WO | WO 2006/02931 A1 | 4/2006 |
| WO | WO 2006/060363 A2 | 6/2006 |
| WO | WO 2007/101016 A2 | 9/2007 |
| WO | WO 2007/132332 A2 | 11/2007 |
| WO | WO2010/084595 A1 | 7/2010 |
| WO | WO2011/069907 A1 | 6/2011 |

OTHER PUBLICATIONS

Cheng, et al.; "Predicting subjective judgment of best focus with objective image quality metrics"; Journal of Vision; Apr. 23, 2004; vol. 4(4); pp. 310-321.

Churms, P.W., "The Theory and Computation of Optical Modifications to the Cornea in Refractive Keratoplasty," American Journal of Optometry & Physiological Optics, 56:2, pp. 67-74, Feb. 1979.

Dymax; UV curable optical assembly; 2 pages; retrieved Mar. 4, 2015 from the internet (http:www.dymax.com/index.php/adhesives/optical).

Huang et al.; Mathematical Model of Corneal Surface Smoothing After Laser Refractive Surgery; American Journal of Ophthalmology; Mar. 2003; pp. 267-278.

Lang, A.J. et al., "First order design of intracorneal inlays: dependence on keratometric flap and corneal properties," ARVO Abstracts 2006, poster No. 3591, May 3, 2006.

Liou, H. L. et al., "Anatomically accurate, finite model eye for optical modeling", Journal of the Optical Society of America, vol. 14, No. 8, Aug. 1997.

Jankov et al.; Laser intrastromal keratoplasty—case report; J. Refract.Surg.; 20(1); pp. 79-84; Jan.-Feb. 2004.

Marsack, et al.; "Metrics of optical quality derived from wave aberrations predict visual performance"; Journal of Vision; Apr. 23, 2004; vol. 4(4); pp. 322-328.

Navarro et al.; Accommodation-dependent model of the human eye with aspherics; J. Opt. Soc Am. A; vol. 2; No. 8; Aug. 1985; pp. 1273-1281.

Patel et al.; Refractive index of human corneal epithelium and stroma; J. Refract. Surg.; 11(2); Abstract; Mar. 1995 (abstract only).

Watsky, M.A. et al., "Predicting Refractive Alterations with Hydrogel Keratophakia," Investigative Opthalmology & Visual Science, vol. 26, pp. 240-243, Feb. 1985.

Winn et al.; Factors affecting light-adapted pupil size in normal human subjects; Investigative Ophthalmology and Visual Science; 35(3); pp. 1132-1137; Mar. 1994.

Sharma et al.; U.S. Appl. No. 14/211,714 entitled "Pre-treatment haze reduction for corneal inlays," filed Mar. 14, 2014.

Daxer et al.; Collagen fibrils in the human corneal stroma: Structure and aging; Ivest Opthalmol & Vis Sci.; 39(3); pp. 644-648; Mar. 1998.

Spector; Chapter 58: The Pupils; in Clinical Methods: The history, physical, and laboratory examinations; Butterworth Publishers; 3rd Edition; 8 pgs; retrieved from the internet (https://www.ncbi.nlm.nih.gov/books/NBK381/); published Jul. 1990.

Plambeck et al.; U.S. Appl. No. 15/163,610 entitled "Corneal implant storage and delivery devices," filed May 24, 2016.

\* cited by examiner

SECTION D-D

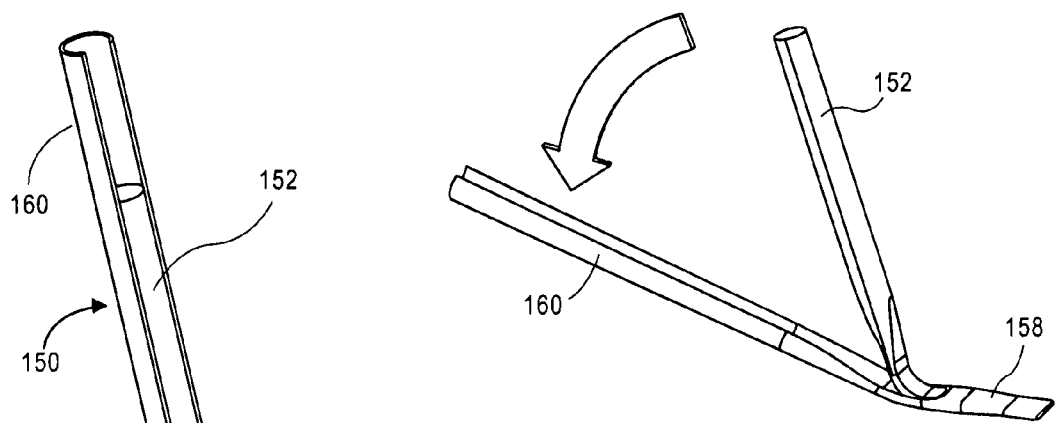
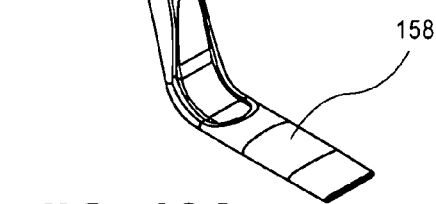
FIG. 12A
FIG. 12B
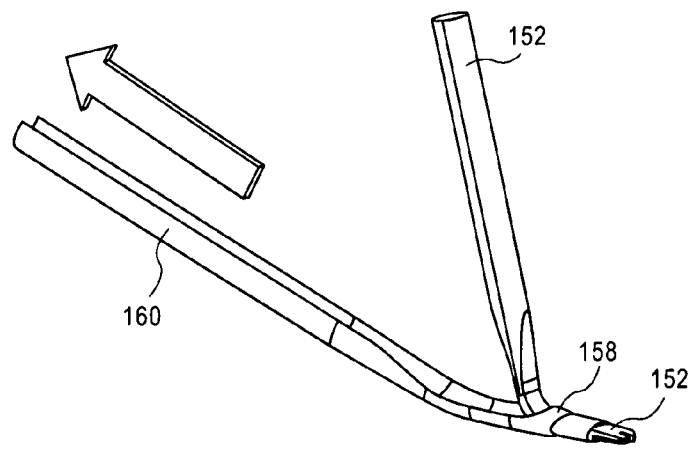
FIG. 12C

CORNEAL IMPLANT RETAINING DEVICES AND METHODS OF USE

CROSS REFERENCE TO RELATED APPLICATIONS

This application is a division of U.S. application Ser. No. 13/549,007, filed Jul. 13, 2012, now U.S. Pat. No. 9,271,828, which is incorporated by reference herein.

Application Ser. No. 13/549,007 also claims the benefit of U.S. Provisional Application No. 61/535,819, filed Sep. 16, 2011, which is incorporated by reference herein.

This application is also related to and incorporates by reference herein the following applications: U.S. Provisional Application No. 61/535,744, filed Sep. 16, 2011; U.S. Provisional Application No. 61/550,185, filed Oct. 21, 2011; and U.S. Provisional Application No. 61/606,674, filed Mar. 5, 2012.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The disclosure herein relates generally to storage and retention devices for corneal implants. During storage, or just prior to use, some corneal implants need to remain hydrated, and yet must be easily removed from storage without being damaged. Some corneal implants can be very light in mass and tacky, or sticky. When preparing the implants for use, there may be one or more components of a storage and/or shipping assembly that are removed relative to the implant delivery device to allow access to the implant. This removal step can prematurely dislodge the implant from its position before it is intended to be moved. Additionally, some implants are stored in a storage solution, such that removal of the storage component can cause the implant to be prematurely drawn out of the delivery device due to cohesive forces between fluid molecules and due to adhesion forces between the fluid and the implant.

SUMMARY OF THE DISCLOSURE

One aspect of the disclosure is a cornea implant insertion system, comprising: a corneal implant insertion device comprising a corneal implant holding area adapted to receive a corneal implant; and a cap adapted to be disposed over at least a portion of a distal region of the insertion device, the cap and the insertion device defining a fluid space in which a fluid is maintained, wherein the cap comprises an opening in fluid communication with the fluid space.

In some embodiments the cap includes a fluid channel extending therethrough in fluid communication with the opening and the fluid space.

In some embodiments the opening is disposed at a distal end of the cap. The cap can have a distal flat face wherein the opening is disposed in the distal flat face. The cap can further include a channel extending from the opening to the fluid space.

In some embodiments the cap has a generally cylindrical configuration. The distal region of the insertion device can have a generally flat configuration.

In some embodiments the cap includes a channel extending from the opening to the fluid space. The cap can include an inner surface adapted to prevent the corneal implant from escaping the holding area. The channel can extend from the opening to the inner surface.

In some embodiments the cap completely surrounds the distal region of the insertion device.

In some embodiments the holding area is defined by a first surface and a second surface of the insertion device. The first and second surfaces can be generally flat surfaces.

In some embodiments the system further comprises a corneal implant disposed within the holding area. The system can also include a second fluid disposed within the holding area and adapted to retain the corneal implant within the holding area by capillary forces. The fluid and the second fluid can be the same type of fluid, such as saline.

In some embodiments the cap comprises an inner surface adapted to engage the distal end of the insertion device and prevent the corneal implant from escaping the holding area.

One aspect of the disclosure is a method of removing fluid from a corneal implant insertion device prior to implanting the corneal implant, comprising: providing a corneal implant insertion device and a cap disposed over at least a portion of a distal region of the insertion device, a first portion of the cap and a first portion of the distal region of the insertion device defining a fluid space in which a fluid is maintained; removing at least a portion of the fluid from the fluid space through an opening in the cap; and removing the cap from the distal region of the insertion device to provide access to a cornea implant retained by the insertion device.

In some embodiments the removing step comprises positioning an absorbent material adjacent the opening to withdraw fluid through the opening.

In some embodiments the removing step comprises aspirating the fluid from the fluid space through the opening with an aspiration device.

In some embodiments the removing step comprises removing at least a portion of the fluid from the fluid space without removing all of a fluid disposed within the insertion device.

In some embodiments the removing step comprises removing at least a portion of the fluid from the fluid space through a channel in the cap. The removing step can comprise inserting an aspiration device within the channel and aspirating the fluid from the space with the aspiration device.

In some embodiments the method further comprises removing the corneal implant from the insertion device and depositing the corneal implant onto corneal tissue.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 12A-12E illustrate an exemplary embodiment of a cap.

DETAILED DESCRIPTION

The disclosure relates generally to storage and retention devices for corneal implants. The devices can be used for long term storage of a corneal implant, or can be used for short term storage, such as just prior to an implantation procedure of the corneal implant. "Corneal implants" used herein refers to any medical device positioned on or in a cornea, and includes, without limitation, corneal inlays, corneal onlays, and contact lenses.

Figure 1:
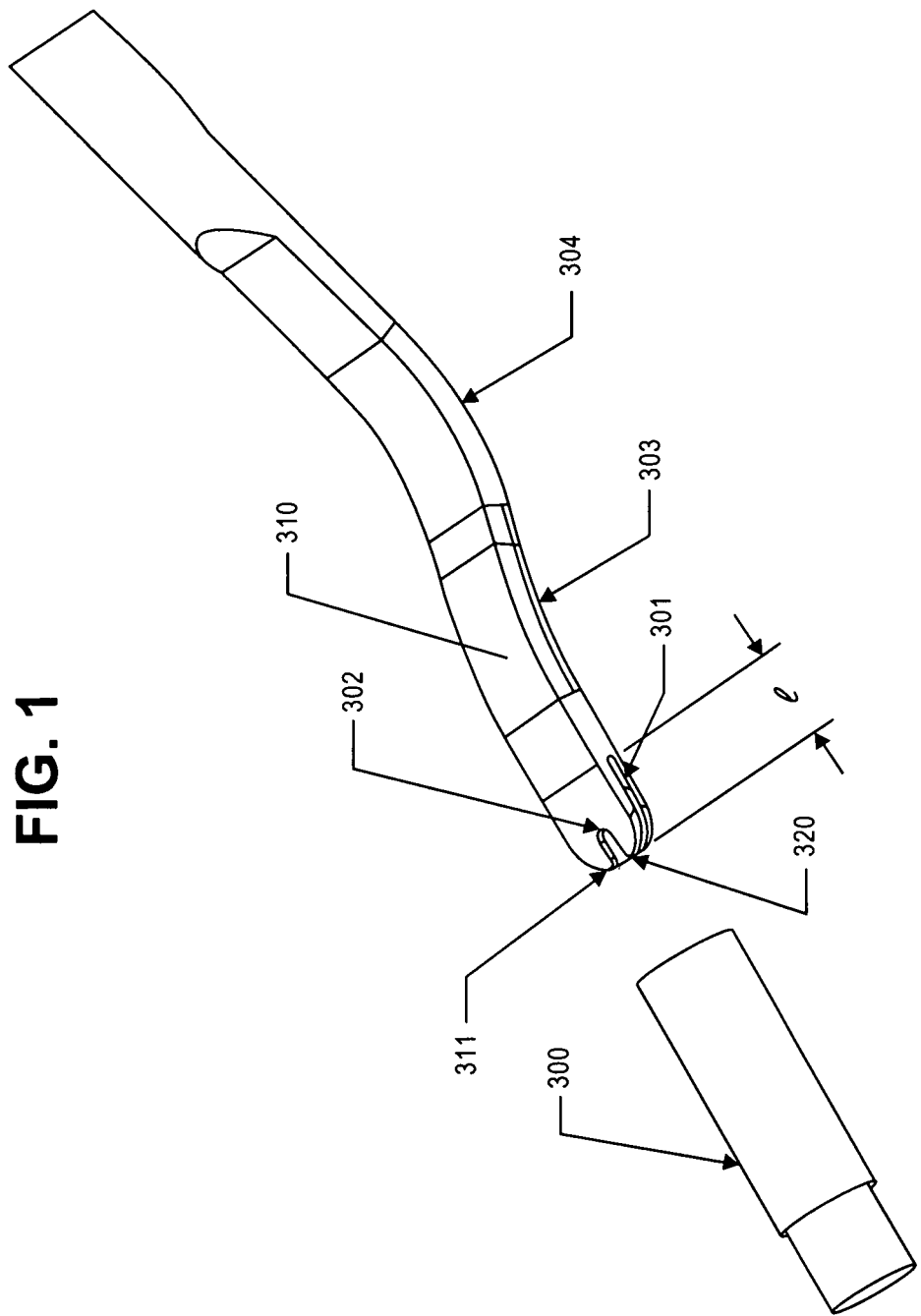
FIGS. 1 and 2 illustrate an exemplary corneal implant insertion device and an exemplary cap.
Figure 2:
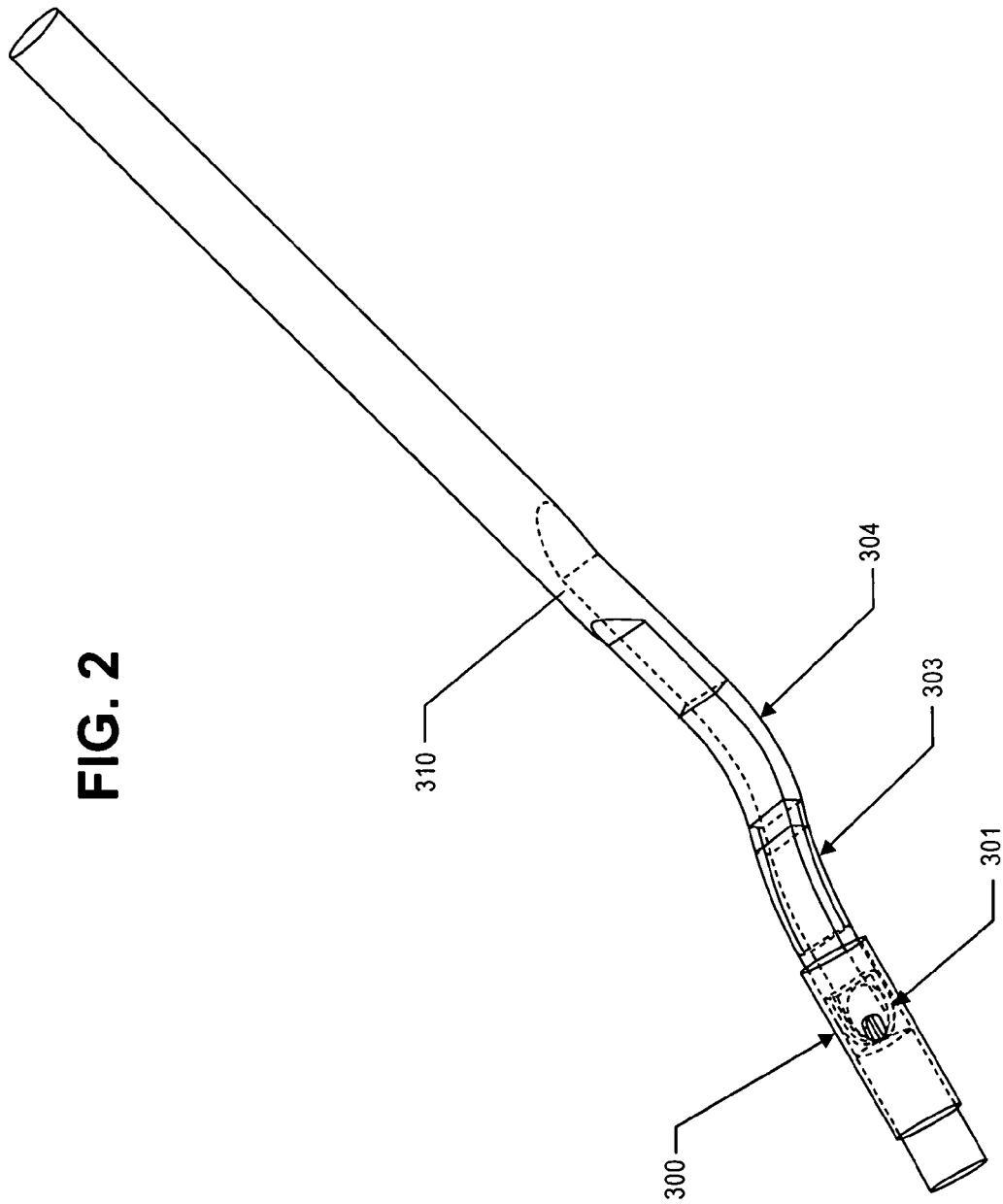

FIGS. 1 and 2 illustrate an exemplary insertion system that is adapted to deliver a corneal implant, e.g., cornea inlay, in or on the cornea. The insertion system can also be used to store the corneal implant prior to its use. The insertion system includes an inserter 310 having an elongated body, which may be made of titanium, stainless steel, plastic, or other biocompatible material. The inserter 310 comprises a distal portion having generally flat top and bottom surfaces. The distal portion of the inserter 310 includes a clearance bend 304 where the inserter is bent to provide clearance between the inserter and a patient's facial features (e.g., nose, cheeks, etc.). The distal portion of the inserter 310 also includes a curved portion 303 that is contoured to follow the shape of a patient's cornea as explained further below. The curved portion 303 is concaved on the bottom surface of the inserter 310.

The inserter 310 additionally includes a holding space 301 adapted to hold a corneal implant 320 to be delivered by the inserter. A fluid such as saline, BSS, or other solution (not shown) is disposed in the holding space 301 to hold implant 320 therein due to surface tension of the fluid. The fluid stays in the holding space 301 due to capillary forces, thereby keeping the implant hydrated. The inserter also includes top inserter slot 302 and a bottom inserter slot (not shown). In addition, the top inserter slot 302 allows the surgeon to hold down the implant 320 in the holding space 301 at a desired position while the surgeon retracts the inserter 310 to release the implant 320. The surgeon may hold down the implant 320 with a surgical tool, such as a cannula, Sinskey hook or other tool that is adapted to fit through top inserter slot 302. Top inserter slot 302 extends to leading edge 311 of inserter 310 so that the tool can hold down implant 320 as the inserter 310 is retracted. Leading edge 311 of the inserter is preferably rounded to prevent damage to the cornea. Exemplary dimensions and additional exemplary features of the inserter shown in this exemplary embodiment can be found in U.S. application Ser. No. 11/692,835, now U.S. Pat. No. 8,162,953. The geometry of holding space 301 and the surface tension of the fluid in holding space 301 keep implant 320 substantially centered in inserter 310. The height of holding space 301 may be several times larger than the center thickness of implant 320 to ensure that enough saline is in holding space 301 to keep the implant sufficiently hydrated.

The inserter system additionally includes cap 300 that is adapted to be disposed over at least a portion of the distal portion of the inserter. FIG. 2 illustrates cap 300 positioned over the distal portion such that cap 300 is disposed over holding space 301 in which a corneal implant is retained.

In some embodiments, inserter cap 300 has a generally cylindrical shape and is adapted to be fitted snugly on the distal end of inserter 310 such that it engages the sides of inserter 310 as shown in FIG. 2. In some embodiments the cap is made of Teflon (PTFE).

In some embodiments, implant 320 is preloaded in inserter 310 and packaged for later use. In one embodiment, implant 320 is preloaded into holding space 301 of inserter 310 with the top surface of implant 320 orientated to face the top surface of inserter 310. Implant 320 may be preloaded by submerging both implant 320 and holding space 301 of inserter 310 in a solution, e.g., saline, and inserting implant 320 into holding space 301 while they are both submerged. After implant 320 is loaded in inserter 310, cap 300 is placed on the distal end of inserter 310. Cap 300 may be placed on inserter 310 while holding space 301 is still submerged in the solution. The preloaded inserter 310 assembled with cap 300 can then be positioned into a vial or other storage container filled with saline or other suitable solution. Cap 300 prevents implant 320 from moving out of inserter 310 when placed in the storage container filled with fluid. The storage container can then be capped and placed in an outer package, which can then be sterilized to store the insertion system until use. The assembled cap and inserter need not, however, be stored in any kind of storage container.

A full exemplary implantation procedure can be found in U.S. application Ser. No. 11/692,835, now U.S. Pat. No. 8,162,953, which is incorporated by reference herein. As a part of that procedure, the preloaded inserter 310 is first removed from a storage container filled with a storage solution. There will be a certain volume of fluid within the space between cap 300 and inserter 310 after it is removed from the storage container. The fluid within the space between cap 300 and inserter 310 is then removed by placing a sterile surgical sponge (not shown) or other absorbent material on the open distal end of cap 300. The absorbent material draws out the saline from the interior of cap 300 by capillary action in the space between the inner surface of cap 300 and inserter 310. In embodiments in which cap 300 has a generally cylindrical shape, the space is defined by inner surface of cap 300 and the flat top and bottom surfaces of inserter 310. The saline is removed from the space between cap 300 and inserter 310 while cap 300 is still on inserter 310. If the cap is removed from inserter before the fluid is removed, cap 300 may pull implant 320 out of the holding space by capillary action when cap 300 is removed from inserter 310. After the fluid is removed, cap 300 is then pulled off of inserter 310. At this point in the process, a small amount of fluid (e.g., saline or BSS) may be applied to holding space 301 of inserter 310 to keep implant 320 hydrated. The fluid stays in holding space 301 due to capillary forces, thereby keeping implant 320 hydrated during the procedure. Further, the surface tension of the fluid holds implant 320 in holding space 301 of inserter 310 so that implant 320 does not fall out of inserter 310 during the procedure. The surface tension and the geometry of holding space 301 keep implant 320 centered in inserter 310. Additionally exemplary features of inserter 310, other exemplary insertion devices, and their methods of use can be found in U.S. application Ser. No. 11/692,835, now U.S. Pat. No. 8,162,953.

Figure 3A:
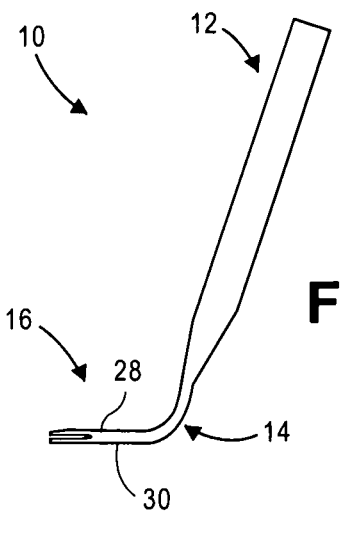
FIGS. 3A-3E illustrate an exemplary corneal implant insertion device.
Figure 3C:
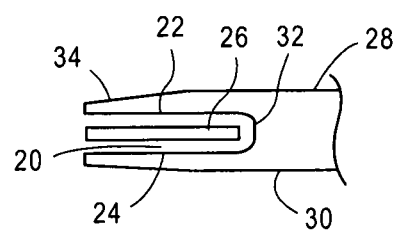
Figure 3B:
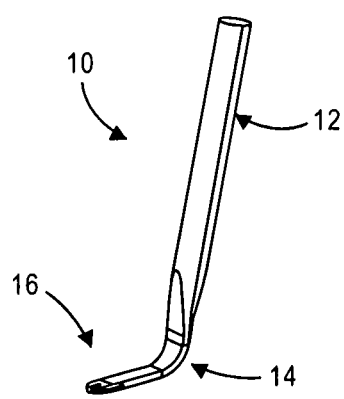
Figure 3D:
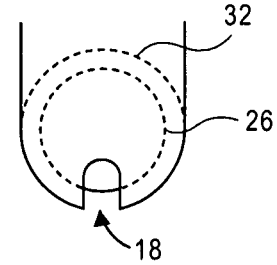
Figure 3E:
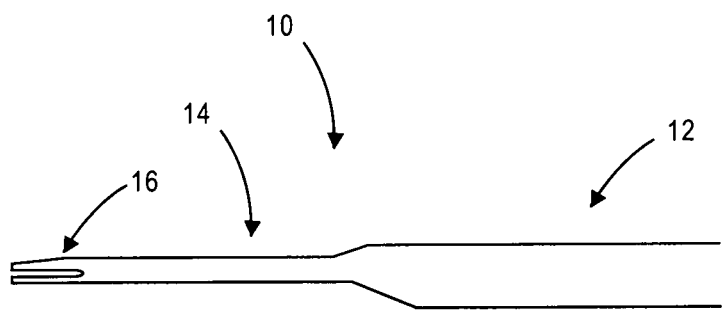

FIGS. 3A-E illustrate a merely exemplary implant delivery device and a merely exemplary corneal implant disposed therein. Delivery device 10 includes distal portion 16, intermediate portion 14, and proximal portion 12. Distal portion 16 includes holding region 20 (see FIG. 3C), in which implant 26 is disposed. A fluid is also disposed within holding region 20 such that implant 26 is retained within holding area 20 by capillary forces. The fluid keeps the implant fully hydrated until it is ready to be delivered into or onto the eye. Holding region 20 is defined by upper surface 22, lower surface 24, and proximal surface 32, as shown in FIGS. 3C (side view) and 3D (top view). Distal region 16 has a generally flat configuration. Upper surface 28 is substantially flat, with surface 34 tapering slightly downwards towards the distal end of distal portion 14. Bottom surface 30 is substantially flat and extends from the bend in intermediate region 14 all the way to the distal end of distal portion 16. Additional details of this embodiment are described in U.S. Provisional Application No. 61/535,744, filed Sep. 16, 2011, the disclosure of which is incorporated by reference herein.

In this embodiment holding area 20 and implant 26 are sized and shaped such that implant 26 is disposed within holding area 20 in a non-deformed, or non-stressed, configuration, and is retained therein due to capillary forces. The non-deformed configuration is substantially the same configuration that the implant is in after it is positioned in or on the subject's corneal. Any of the caps described herein can be used with the insertion device of FIGS. 3A-3E to help retain the corneal implant in the insertion device.

Figure 4:
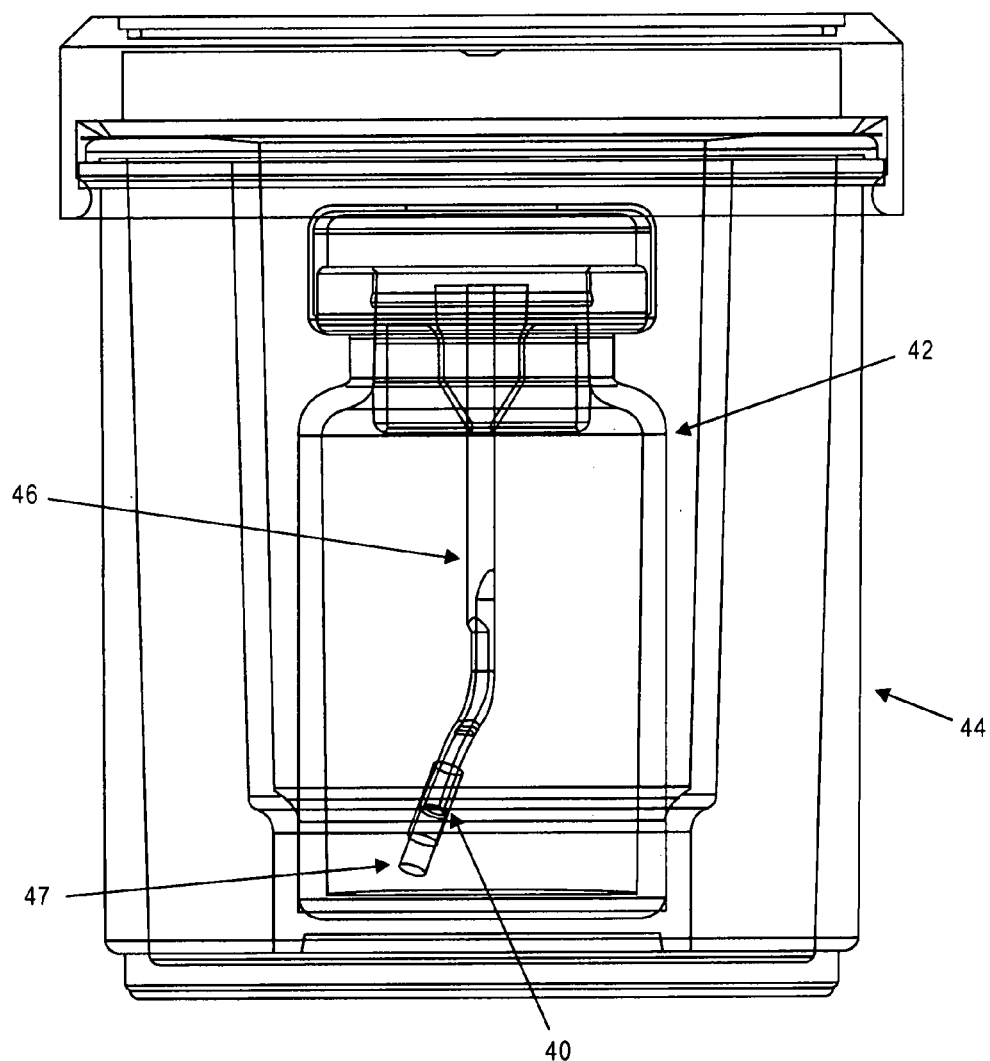
FIG. 4 illustrates an exemplary storage container inside exemplary outer packaging.

During storage, it is generally beneficial for an additional device to be positioned with respect to the delivery device (or other storage component) and inlay to retain the inlay within the holding space of the delivery device. Cap 300 from the embodiment in FIGS. 1 and 2 above is example of such an additional device. FIG. 4 illustrates a merely exemplary storage container 42 inside outer packaging 44. Inlay holder 46, with inlay 40 therein, is stored in storage container 42, which includes a cap and is filled with a storage fluid such as saline. To retain inlay 40 within inlay holder while stored in the fluid filled storage container, retaining element 47 is disposed over the distal end of inlay holder 46.

Figure 5:
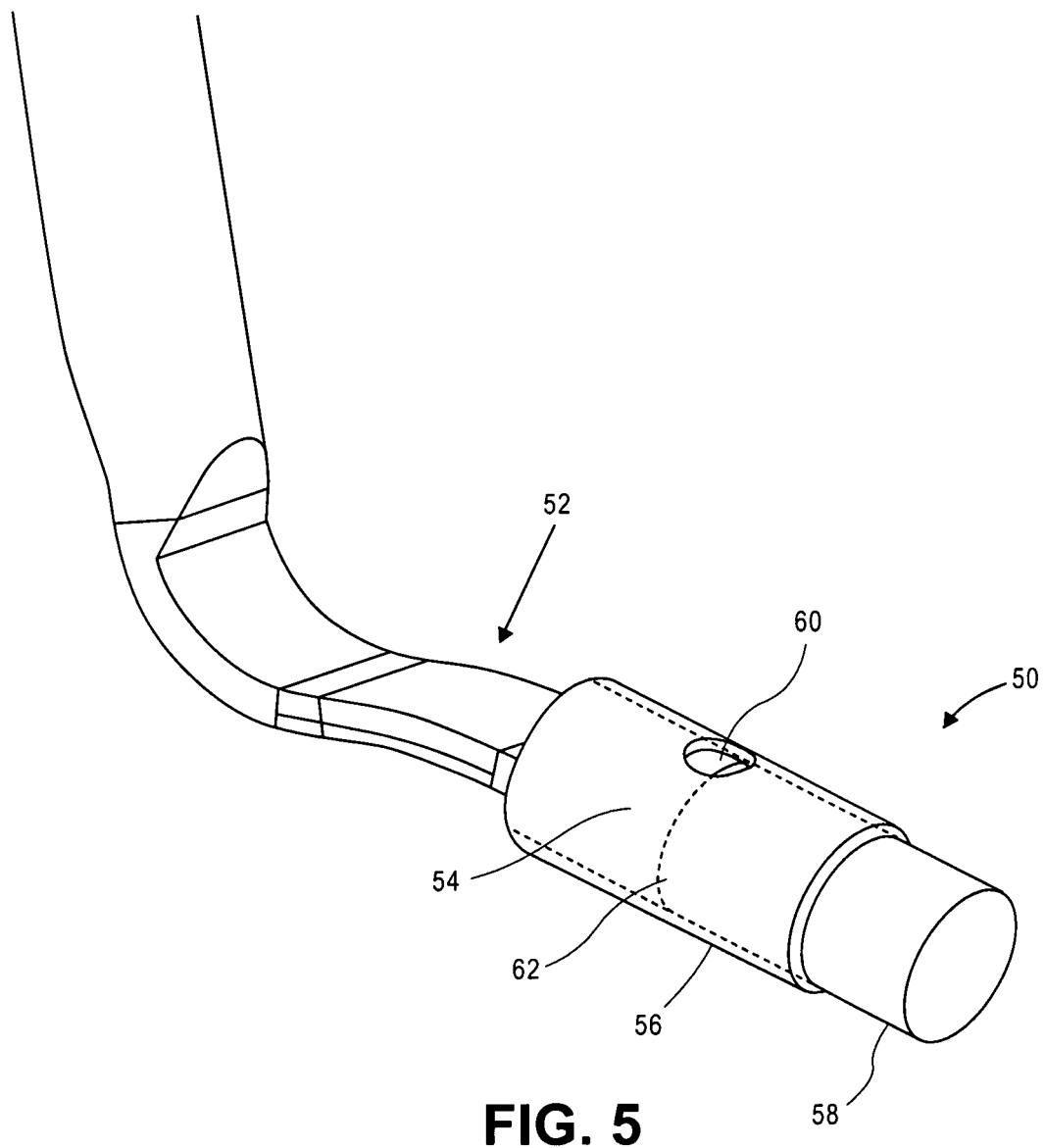
FIG. 5 illustrates an exemplary cap.

FIG. 5 illustrates an exemplary embodiment of retaining device 50, in the form of a cap, disposed over the distal portion of corneal inlay holder 52 to retain inlay 54 within the holding space in the distal portion of the inlay holder. The holding space and inlay are substantially similar to those in the embodiment described above in FIGS. 1 and 2. Retaining device 50 is in the form of a cap and includes outer element 56 and inner element 58 partially disposed within outer portion 56. Inner element 58 includes a proximal surface 62 that is in contact with the very distal end of inlay holder 52. Proximal surface 62 prevents inlay 54 from escaping from inlay holder 52. To store the inlay, retaining cap 50 is placed over the distal end of holder 52 after the inlay is positioned therein. The assembly is then placed in a storage container filled with a storage solution, such as container 42 in FIG. 4. Bores 60 (one is on the underside in FIG. 3) in outer element 56 allow fluid to pass into the space between inlay holder 52 and retaining device 50 to keep the inlay fully hydrated while stored in a storage container. In one embodiment cap is made from Teflon (PTFE). The inner and outer elements can be two components that are, for example, press fit together, or they can be a molded part.

Before the implant can be implanted, the retaining device must be removed from the distal end of the inlay holder to allow access to the implant. When removing the retaining element, however, surface tension cohesive forces between fluid molecules can cause the fluid within the holding space to be pulled from the holding space. Additionally, adhesion forces between the fluid and the inlay can also draw out the inlay from the holding space as the retaining element is removed. Removing the retaining element can therefore prematurely pull the inlay from the holding space before the intended time. To prevent any of these from occurring, fluid between retaining element 50 and inlay holder 52 can be removed (also referred to herein as "aspirated" and "evacuated") by a suitable fluid removal technique prior to removing retaining element 50. For example, the fluid can be evacuated by positioning an absorbent material such as a sponge against bore 60, such as is described in the embodiment in FIGS. 1 and 2 above. Fluid will be drawn from the enclosure and into the sponge, removing the fluid from the enclosure. Exemplary absorbent materials include Weck-cell eye spears. Alternatively, a cannula, syringe, or aspiration needle can be positioned adjacent to or within bore(s) 60 and used to aspirate the fluid through bore 60. The fluid within the holding space of the implant holder, however, needs to be retained therein to keep the implant fully hydrated until it is time for delivery into or onto the eye.

Figure 6:
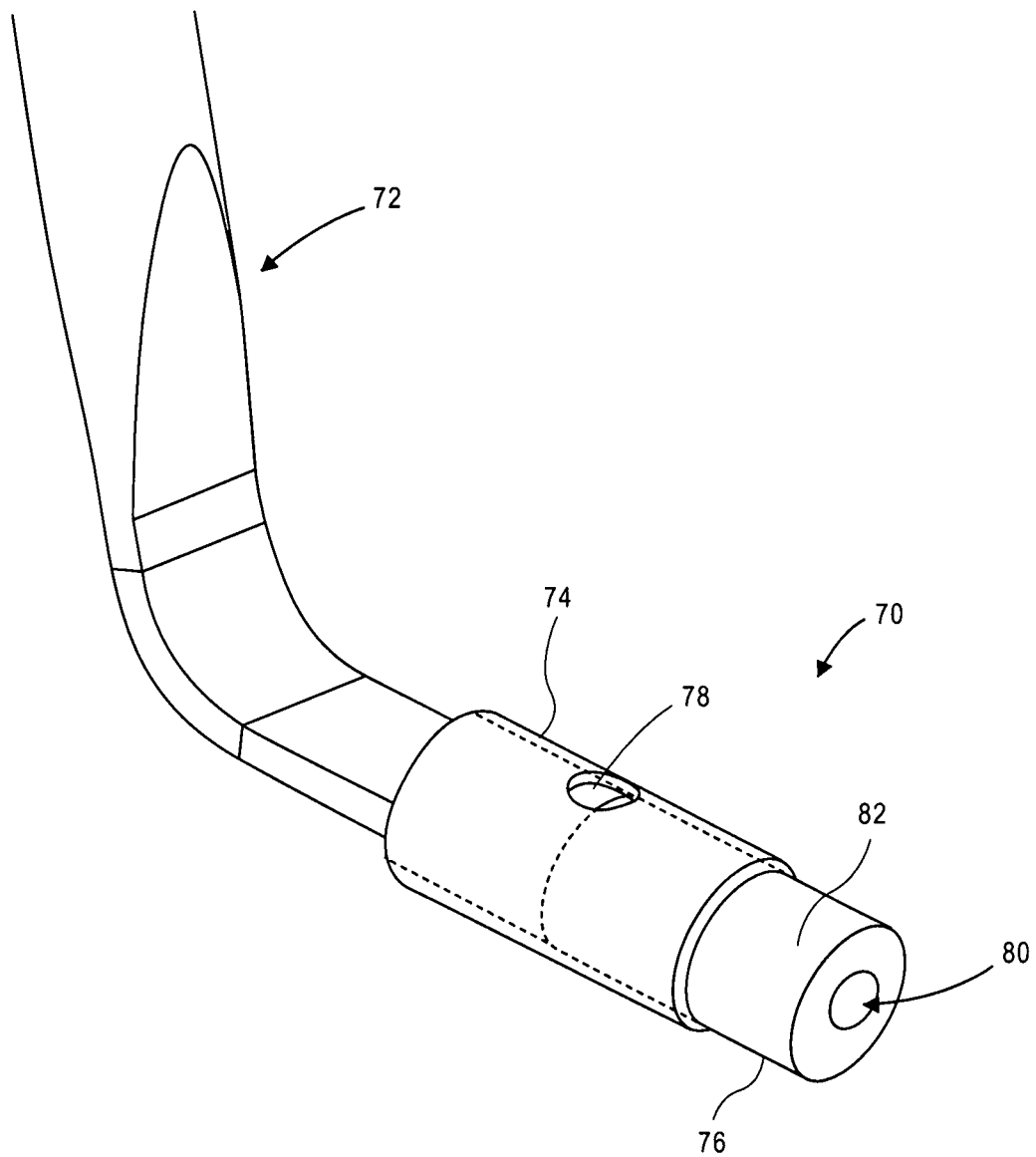
FIG. 6 illustrates an exemplary cap.

FIG. 6 illustrates an alternative embodiment of retaining device 70. Retaining device 70 includes outer tubular element 74 and inner element 76. Outer element 74 includes bores 78 (one on the underside). Inner element 76 has a channel 82 running along its length, fluidly connecting the enclosure between device 70 and inlay holder 72, and opening 80. The inner element has a proximal surface as in the embodiment in FIG. 5 that prevents the inlay from escaping the holding space of the inlay holder 72. As in the embodiment in FIG. 5, any suitable technique can be used to remove fluid from the enclosure prior to removing retaining element 70 from inlay holder 72, such as using an absorbent material, or using an aspiration device such as an aspiration needle. Fluid can be removed via opening and/or bores 78. Fluid can be removed through channel 82 out of opening 80. Fluid can also be removed from bores 78.

Figure 7:
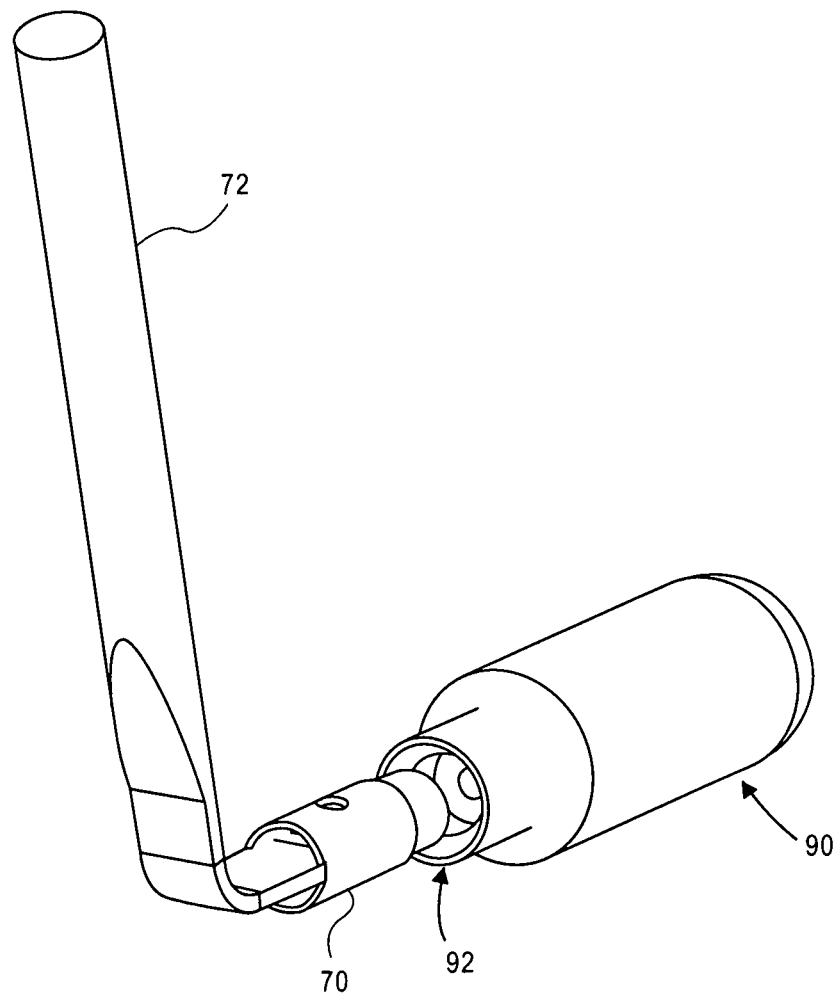
FIG. 7 illustrates an exemplary device for removing fluid from a fluid space.

FIG. 7 illustrates an additional exemplary technique for removing the fluid from enclosure before removing the retaining element. Dropper bulb/vacuum pump 90 is adapted to engage an outer surface of inner element 76 of retaining device 70, as shown in FIG. 6. In use, a user first compresses the bulb to remove air from the bulb. The dropper bulb is then fitted over inner element 76 of retaining device 70. The force on the bulb is released, drawing the fluid from the enclosure into the dropper bulb. The bulb can be adapted such that only a certain amount of fluid can be removed from the inserter, which can prevent fluid from being removed from the holding space.

Inner channel 82 within inner element 76 is small enough that the corneal implant is prevented from escaping from the holding space (due to the proximal surface of the inner element with the channel opening therethrough), yet allows fluid to be removed from the enclosure when needed.

It may be better to have as short an inner channel 82 as possible, to ease the fluid removal. In some embodiments the inner element 76, and therefore channel 82, are between about 0.05 inches and about 0.25 inches in length. In some embodiment the channel is about 0.15 inches in length. Inner and outer elements 76 and 78 can be made from Teflon and are press fit together. Alternatively, they can be a single-piece molded component.

Figure 8A:
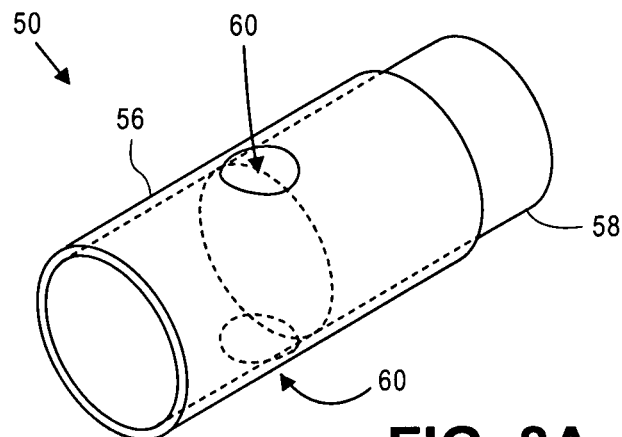
FIGS. 8A-8D illustrate views of an exemplary cap.
Figure 8B:
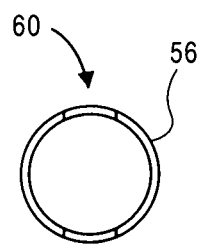
Figure 8C:
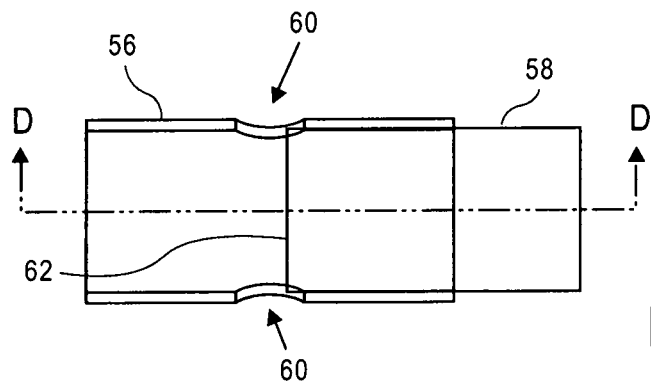
Figure 8D:
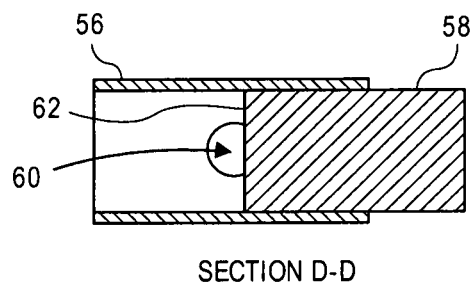

FIGS. 8A-8D illustrate retaining device 50 from FIG. 5. FIG. 8A is a perspective view showing inner and outer elements 58 and 56 respectively, and apertures, or bores, 60 through outer element 56. FIG. 8B is an end view looking though the open end of outer element 56. FIG. 8C is a sectional view, showing proximal surface 62 that abuts against or is adjacent to the distal end of the implant holder to prevent the implant from escaping the holding space. FIG. 8D is a sectional view DD along the plane shown in FIG. 8C.

Figure 9:
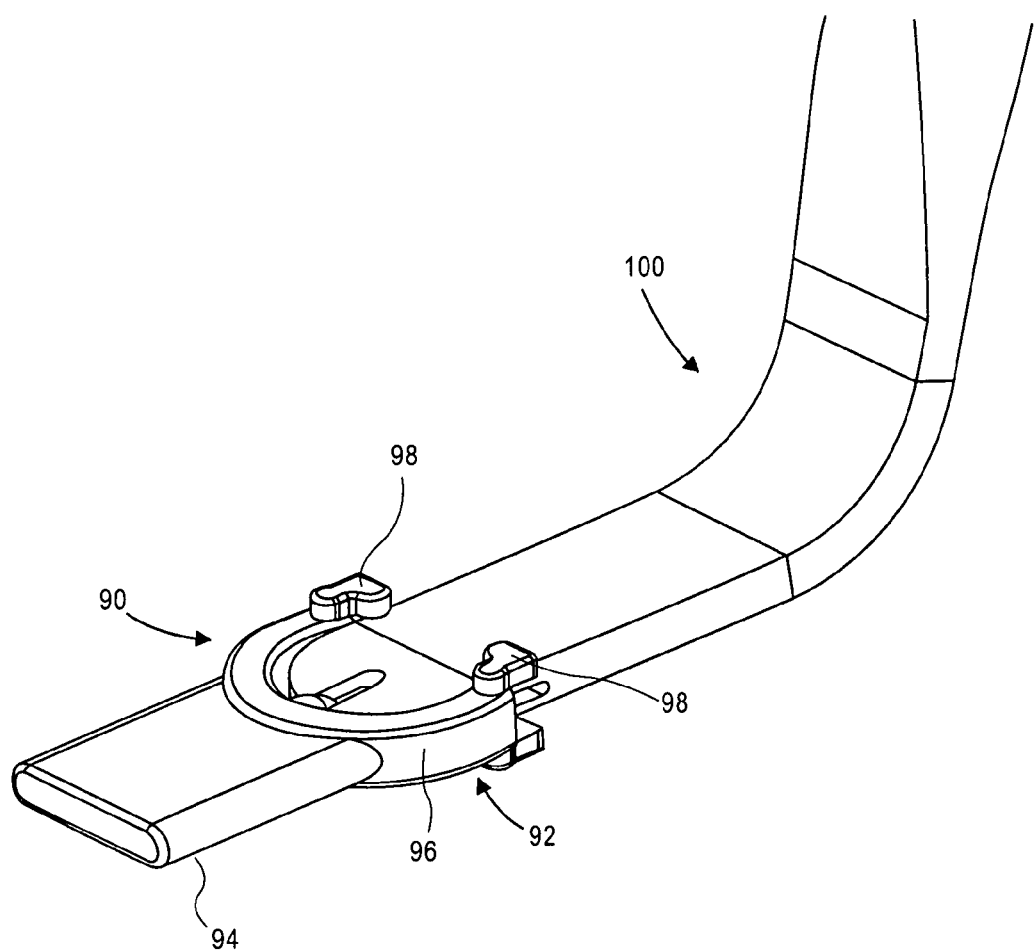
FIGS. 9-10D illustrate an alternative exemplary cap.
Figure 10A:
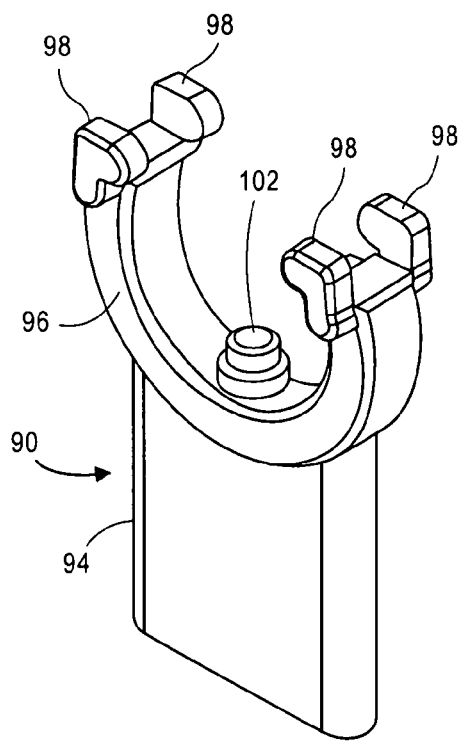
Figure 10B:
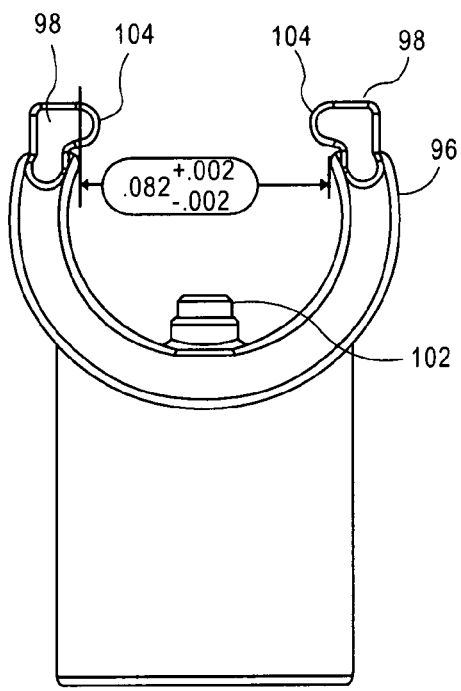
Figure 10C:
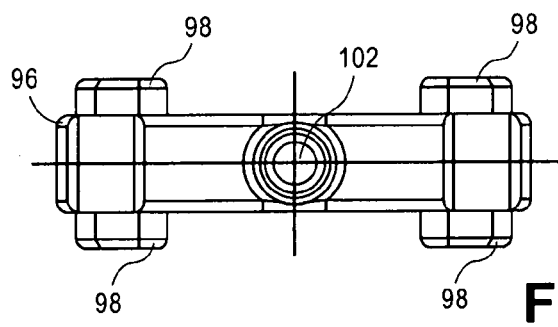
Figure 10D:
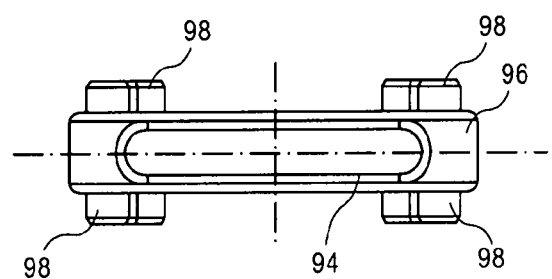

FIG. 9 illustrates an exemplary embodiment of a cap to be placed over the distal end of an implant holder during storage. Retaining element 90 includes cap section 92 coupled to handle 94. Cap section 92 includes a generally C-shaped cap 96 and four end elements 98. Each end element 98 has an extension 104 (see FIG. 10B) adapted to fit over the top and bottom surfaces of the implant holder 100. Cap section 92 also includes boss 102 to retain the corneal implant within the holding space in the implant holder 100. Boss 102 is generally along the centerline of cap 96. FIGS. 10A-10D illustrate views of retaining element 92, with merely exemplary dimensions shown.

When the implant is to be removed from holder 100, retaining element 90 is removed from holder 100. Any of the fluid removal techniques described herein can be used to remove fluid from between the cap/inserter tool before the cap is removed. For example, a sponge can be engaged with the C-shaped cap 96 to absorb excess fluid. In some embodiments the handle is about 1 inch or less in length. In some embodiments it is about 0.5 inches or less.

The retaining device could be further modified such that it is adapted to be rotated upwards or downwards relative to implant holder 100 for removal from holder 100. For example, C-shaped cap 96 can be adapted to rotate up and/or down with respect to end elements 98. Rotating the C-cap upward prevents inadvertent removal of the implant from the retaining device in the horizontal direction due to adhesion forces between the implant, fluid, and the C-cap.

Additionally, cap 96 need not be generally C-shaped with a single radius of curvature, but can have an aspherical and/or asymmetrical configuration.

Figure 11:
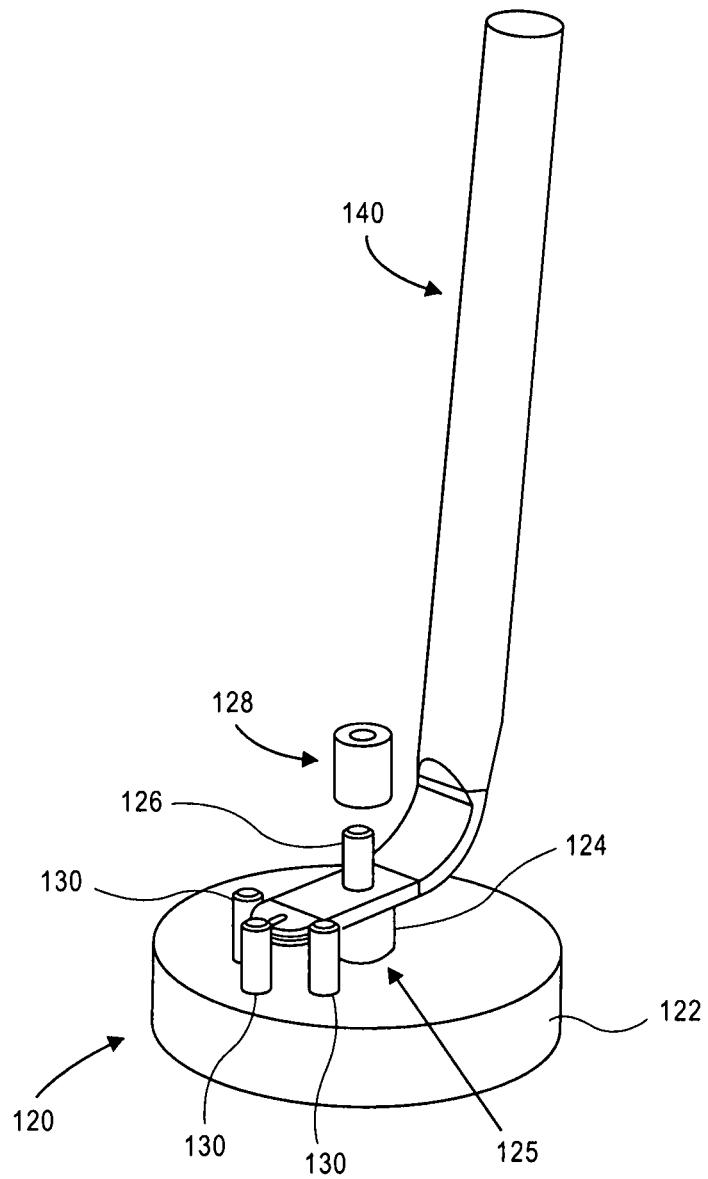
FIG. 11 illustrates an alternative retaining device.

FIG. 11 illustrates an alternative retaining mechanism. Retainer 120 includes base 122 to which are secured three retaining pins 130 and implant holder mount 125, which includes a larger diameter lower portion 124 and a smaller diameter upper pin portion 126. Implant holder 140 has a through-hole therein in the distal portion that is sized to allow upper portion 126 to fit therethrough. Implant holder 140 sits atop lower portion 124. Pins 130 secured to base 122 provide three points of contact around the distal end of implant holder 140 to trap the implant within the holding space as described above. Pin 126 is used to register the implant holder 140 relative to pins 130. Once the holder 140 is loaded onto retaining element 120, the assembly could be placed in a storage container filled with storage solution, such as the one shown in FIG. 4. Alternatively, pins 130 and 126 can be molded into the bottom of the storage container, such that the inlay holder is placed over the pins of the storage container to load implant holder 140 into the storage container. To remove holder 140 from retaining element 120, holder 140 is lifted up relative to base 122 to clear the through-hole from pin 126.

A nest or well could alternatively be used instead of pins 130 to trap the implant.

The disclosure also includes retaining elements, or caps, that are removed in a proximal direction, or away from the distal end of the holding space and towards proximal end of the implant holder. This is generally the reverse direction to that shown in some of the embodiments above, such as in FIGS. 5 and 6. This effectively pulls the implant into, or towards, the holding space as opposed to away from the holding space. Any device that retains the implant within the holding space and is removed in the proximal direction is included within this disclosure.

FIGS. 12A-12E illustrate an exemplary embodiment of a reverse motion retaining element. Reverse-pull sheath 150 includes an elongate handle attachment 160, and retaining portion 158 that covers the distal tip of implant holder 152, which has an implant held therein in a holding space at the distal end as described above. The distal end of retaining portion 158 in this embodiment has a duck bill end that keeps the implant within holder 152. Reverse-pull sheath 150 is formed such that handle portion 160 is held in place wrapped around implant holder 152 until deliberately removed. The sheath conforms to the geometry of implant holder 152. The degree of sheath conformity to the implant holder can control the amount of fluid retained in and on the implant holder and delivered to the stroma bed with the implant. In this embodiment the distal portion 158 is crimped shut, but any closure technique can be used. In this embodiment the sheath is a flexible material such as Teflon.

Figure 12D:
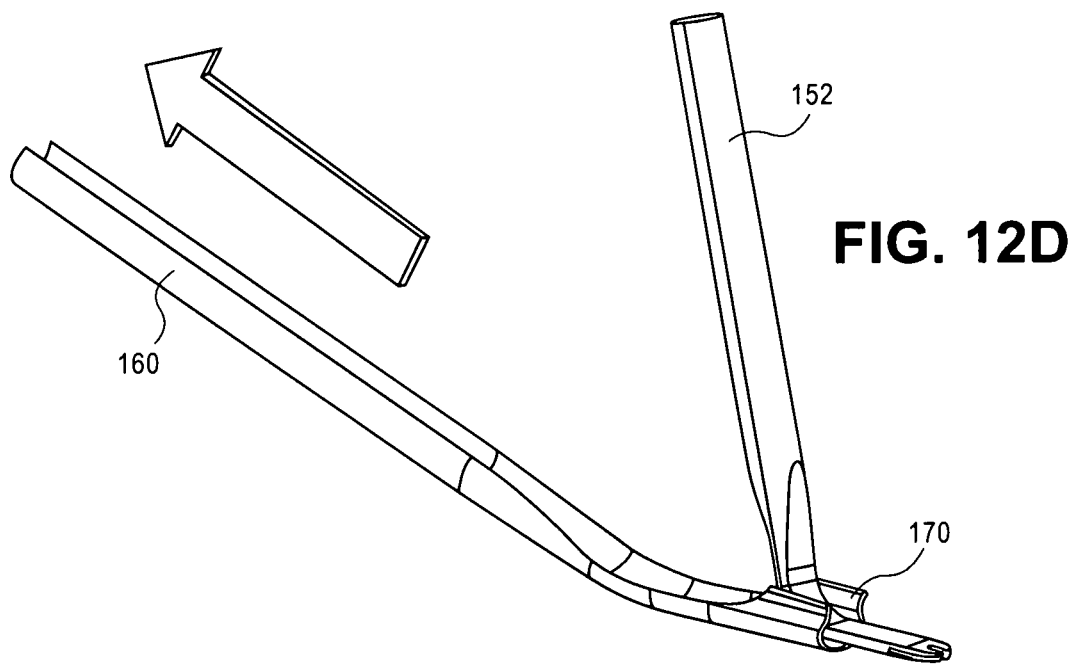
Figure 12E:
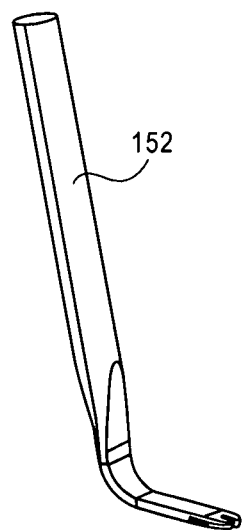
Figures 13A, 13B:
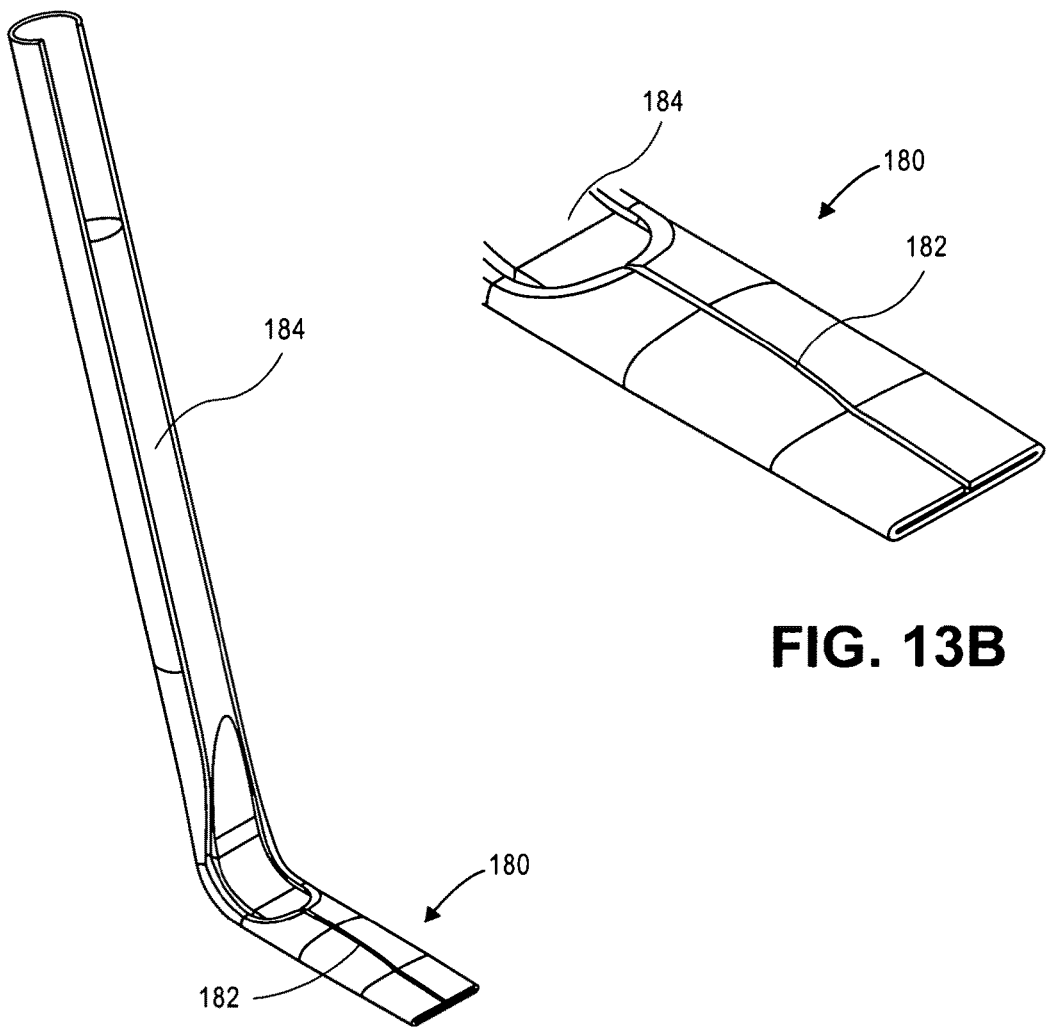
FIGS. 13A-13B illustrate an exemplary embodiment of a cap with a feature to assist in removing the cap from the insertion device.

In use, when the inlay is to be delivered into the eye, the sheath is removed from the inlay holder 152. First, as shown in FIG. 12B, handle portion 160 is pulled back in the direction of the arrow to separate handle portion 160 from inlay holder 152. Next, the sheath is pulled in a general proximal direction away from the distal end of the inlay holder 152, as shown in FIG. 12C. Pulling the sheath in this direction ensures that the implant is retained in the holding space of holder 152. The distal portion 158 of sheath 150 is adapted to tear-away, rupture, break, etc., to allow distal portion 158 to be unwrapped from the distal end of holder 152. The sheath continues to be pulled in a general proximal direction such that distal portion 158 is removed in the proximal direction until the distal portion 158 of sheath is completely torn, as shown in FIG. 12D. To assist in the tearing, the distal portion 158 includes any suitable tearing feature, such as without limitation, one or more perforations or slits. Once the sheath has been completely removed from inlay holder 152, the sheath can be discarded, and the implant holder with implant therein is ready for use. FIGS. 13A and 13B illustrate an embodiment in which the sheath includes slit 182 in the distal portion 180 to assist in the tearing away from implant holder 184. Slit 182 can be continuous, interrupted, perforated, or take any other suitable form.

Figure 14A:
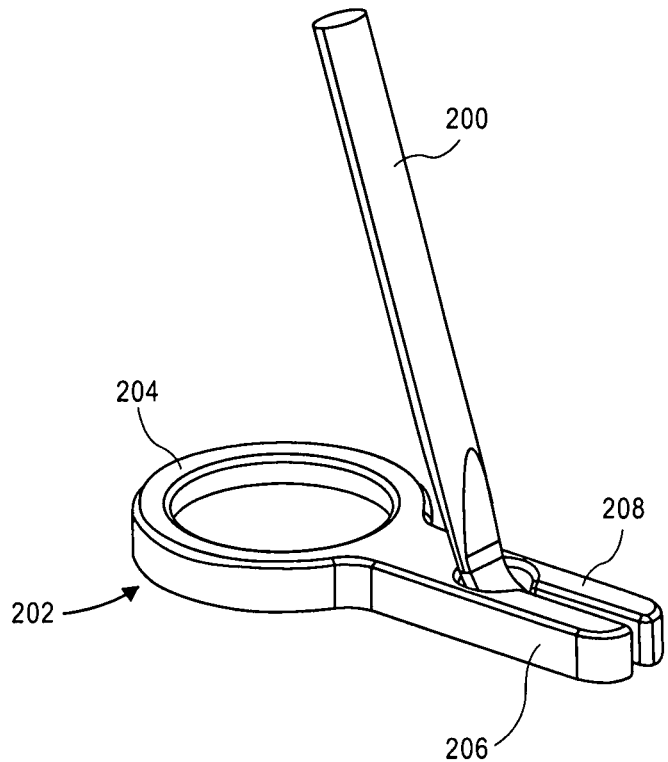
FIGS. 14A and 14B illustrate an alternative embodiment of a cap.
Figure 14B:
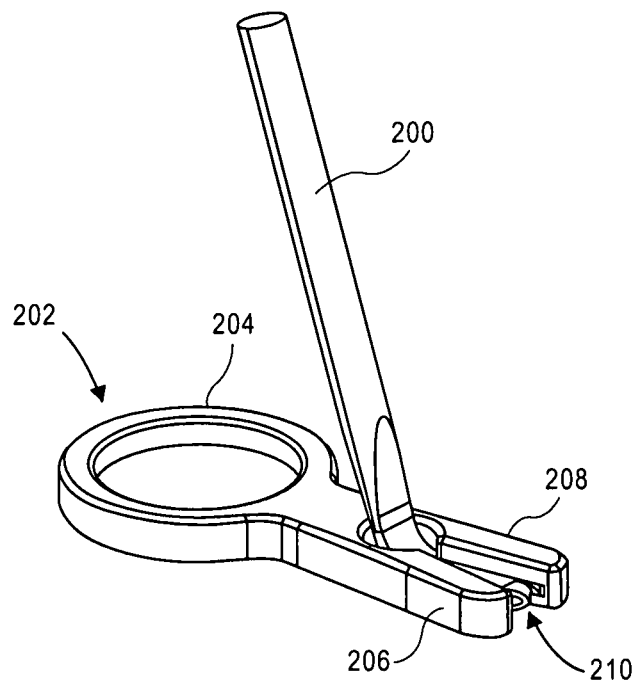

FIGS. 14A and 14B illustrate an alternative embodiment in which retainer 202 includes a pull tab 204 with a generally annular configuration, and a cap portion with cantilevered arms 206 and 208. When the arms are in the storage configuration shown in FIG. 14A, the arms make point contact with the implant to retain in the holding space, but are positioned in an open enough configuration to allow fluid to keep the implant hydrated. When tab 204 is pulled in the direction of the arrow in FIG. 14B (a general proximal direction away from the distal end of implant holder 200), the arms bend away from one another, allowing retainer 202 to be removed from implant holder 200. The implant is then ready for use.

One of the advantages of the reverse-pull embodiments in FIGS. 12A-14B is that fluid does not need to be wicked away, or removed, prior to removal of the retaining element. This can simplify the overall procedure of preparing the implant for use. It is of course understood that this step could, however, still be performed.

Figure 15A:
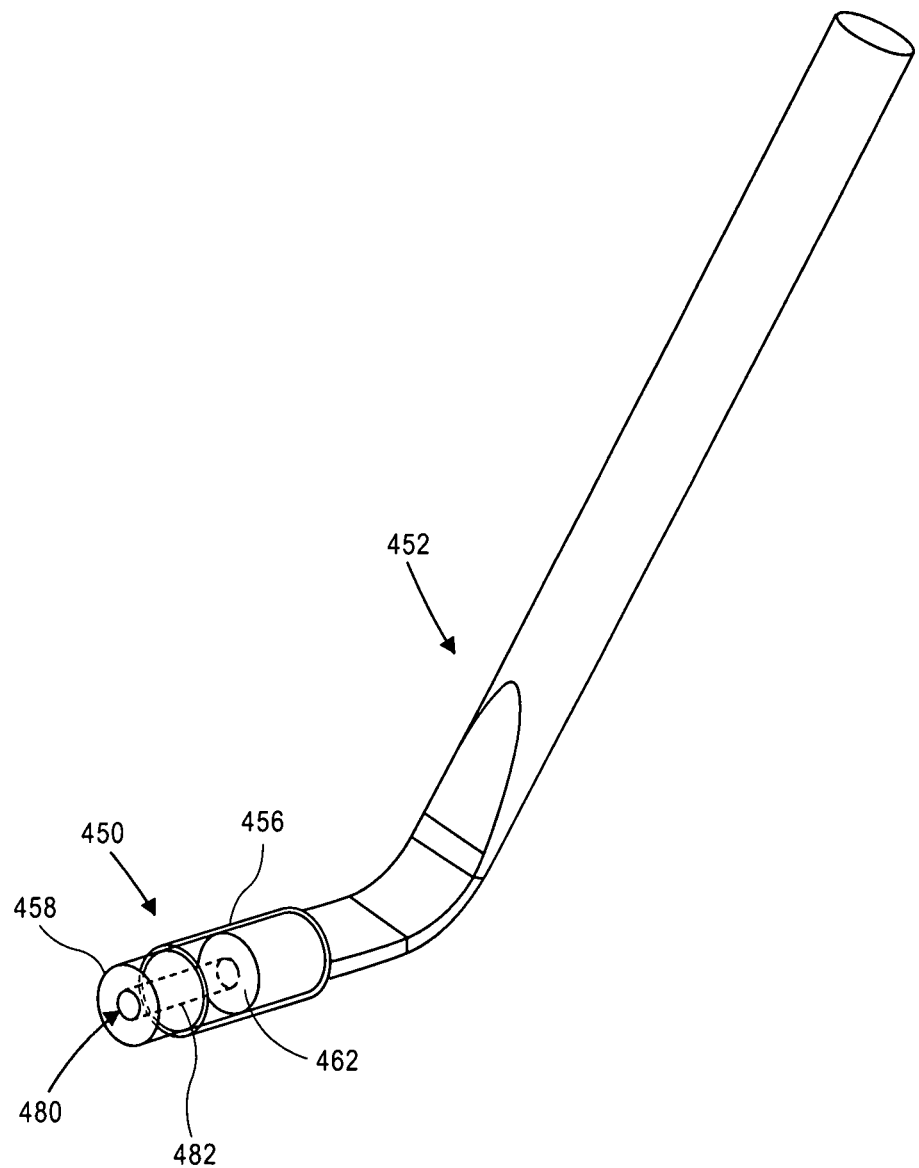
FIGS. 15A and 15B illustrate an exemplary embodiment of a cap.
Figure 15B:
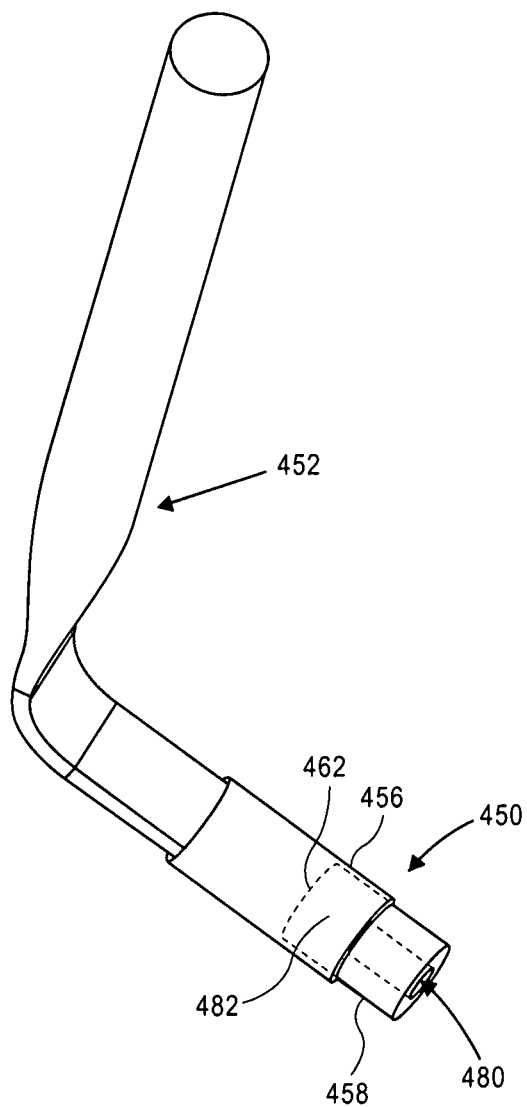

FIGS. 15A and 15B illustrate an exemplary embodiment of an insertion device and a cap similar to those described above with respect to FIGS. 5 and 6. The insertion device, however, is similar to that shown in FIGS. 3A-3E in that the distal region is substantially flat and does not have the additional clearance bend 303, as is found in the embodiment in FIGS. 1 and 2. Retaining device, or cap, 450 is adapted to be disposed over the distal portion of corneal implant holder 452 to retain a corneal implant (not labeled) within the holding space in the distal portion of the inlay holder. The holding space and inlay are substantially similar to those in the embodiment described above in FIGS. 5 and 6. Retaining device 450 is in the form of a cap and includes outer element 456 and inner element 458 partially disposed within outer portion 456. Inner element 458 includes a proximal surface 462 that is in contact with, or directly adjacent to, the distal end of inlay holder 452. Proximal surface 462 prevents the corneal implant from escaping from the holding space within inlay holder 452. Inner element 458 has a channel 482 running along its length, fluidly connecting opening 480 and the space between cap 450 and inlay holder 452. As in the embodiments in FIGS. 5-7, any suitable technique can be used to remove fluid from the enclosure prior to removing retaining element 450 from inlay holder 452, such as using an absorbent material, or using an aspiration device such as an aspiration needle. Fluid is removed via opening 480 and channel 482.

To store the inlay, retaining cap 450 is placed over the distal end of holder 452 after the inlay is positioned therein. The assembly is then placed in a storage container filled with a storage solution, such as container 42 in FIG. 4.

Any other features described above with respect to the caps shown in the embodiments in FIGS. 5 and 6 can be incorporated into the embodiment of the cap shown in FIGS. 15A and 15B.

A retaining element with at least one opening therein can conceivably be used to retain any type of corneal implant in an insertion or delivery device, even if the insertion or delivery device is not described herein.

Any type of corneal implant that is adapted to be received within a holding space of any of the insertion devices described herein (or any other type of insertion or delivery device) can be retained by any of the retaining elements described herein.

Exemplary corneal implants that can be incorporated into the systems described herein can be found described in any the following applications, the disclosures of which are incorporated herein by reference: U.S. application Ser. No. 10/837,402, filed Apr. 30, 2004, now U.S. Pat. No. 7,776,086; U.S. application Ser. No. 11/106,983, filed Apr. 15, 2005; U.S. application Ser. No. 11/554,544, filed Oct. 30, 2006, now U.S. Pat. No. 8,057,541; U.S. application Ser. No. 11/738,349, filed Apr. 20, 2007; U.S. application Ser. No. 12/418,325, filed Apr. 3, 2009, now U.S. Pat. No. 8,900,296; and U.S. application Ser. No. 12/877,799, filed Sep. 8, 2010.

What is claimed is:

1. A corneal implant insertion system, comprising:
   a corneal implant insertion device comprising a corneal implant holding area; and
   a cap adapted to be disposed over at least a portion of a distal region of the insertion device and adapted to be removed from the distal region of the corneal implant insertion device prior to insertion of a corneal implant, the cap and the insertion device defining a fluid space in which a fluid is maintained,
   wherein the cap comprises
      a front end that comprises a distal flat face and
      an opening passing through the distal flat face, the opening in fluid communication with the fluid space,
   wherein the cap has a length less than a length of the corneal implant insertion device, wherein the cap has a proximal end that is disposed distal to a proximal end of the corneal implant insertion device.

2. The system of claim 1 wherein the cap comprises a fluid channel extending therethrough in fluid communication with the opening and the fluid space.

3. The system of claim 1 wherein the cap has a generally cylindrical configuration.

4. The system of claim 3 wherein the distal region of the insertion device has a generally flat configuration.

5. The system of claim 1 wherein the cap includes an inner surface adapted to prevent the corneal implant from escaping the holding area.

6. The system of claim 5 wherein the channel extends from the opening to the inner surface.

7. The system of claim 1 wherein the cap completely surrounds the distal region of the insertion device.

8. The system of claim 1 wherein the holding area is defined by a first surface and a second surface of the insertion device.

9. The system of claim 8 wherein the first and second surfaces are generally flat surfaces.

10. The system of claim 1, wherein the opening is one of a plurality of openings, each of the plurality of openings passing through one of the front end of the cap and the peripheral wall of the cap, each of the plurality of openings being in fluid communication with the fluid space.

11. A corneal implant insertion system, comprising:
    a corneal implant insertion device comprising a corneal implant holding area and a distal region with generally flat top and bottom surfaces; and
    a cap adapted to be disposed over at least a portion of the distal region of the insertion device and adapted to be removed from the distal region of the corneal implant insertion device prior to insertion of a corneal implant, the cap and the insertion device defining a fluid space in which a fluid is maintained, wherein the cap comprises an opening passing through one of a front end of the cap and a peripheral wall of the cap, the opening in fluid communication with the fluid space,
    wherein the cap has a length less than a length of the corneal implant insertion device, wherein the cap has a proximal end that is disposed distal to a proximal end of the corneal implant insertion device.

12. The system of claim 11, wherein the cap comprises a fluid channel extending therethrough in fluid communication with the opening and the fluid space.

13. The system of claim 11, wherein the cap has a generally cylindrical configuration.

14. The system of claim 11, wherein the cap includes an inner surface adapted to prevent the corneal implant from escaping the holding area.

15. The system of claim 11, wherein the cap completely surrounds the distal region of the insertion device.

16. The system of claim 11, wherein the holding area is defined by flat top and bottom surfaces.

17. The system of claim 11, wherein the opening is one of a plurality of openings, each of the plurality of openings passing through one of the front end of the cap and the peripheral wall of the cap, each of the plurality of openings being in fluid communication with the fluid space.

* * * * *